(12) United States Patent
Kang et al.

(10) Patent No.: US 9,778,229 B2
(45) Date of Patent: Oct. 3, 2017

(54) APPARATUS AND METHOD FOR MEASURING NONLINEARITY PARAMETER USING LASER

(71) Applicant: KOREA ATOMIC ENERGY RESEARCH INSTITUTE, Daejeon (KR)

(72) Inventors: To Kang, Suwon-si (KR); Jin-Ho Park, Daejeon (KR); Doo-Byung Yoon, Daejeon (KR); Soon-Woo Han, Hwaseong-si (KR); Jang-Soo Lee, Daejeon (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 266 days.

(21) Appl. No.: 14/632,101

(22) Filed: Feb. 26, 2015

(65) Prior Publication Data

US 2015/0241395 A1 Aug. 27, 2015

(30) Foreign Application Priority Data

Feb. 27, 2014 (KR) ........................ 10-2014-0022991

(51) Int. Cl.
*G01N 29/24* (2006.01)
*G01B 11/16* (2006.01)
(Continued)

(52) U.S. Cl.
CPC ....... *G01N 29/2418* (2013.01); *G01B 11/161* (2013.01); *G01N 29/11* (2013.01);
(Continued)

(58) Field of Classification Search
CPC .... G01N 29/22; G01N 29/043; G01N 29/221; G01N 29/2418; G01N 29/11;
(Continued)

(56) References Cited

U.S. PATENT DOCUMENTS 5,608,166 A * 3/1997 Monchalin ............... G01H 9/00
73/655
2005/0023434 A1* 2/2005 Yacoubian ......... G01N 29/2418
250/200

(Continued)

FOREIGN PATENT DOCUMENTS

| JP | 2009053043 | 3/2009 |
|---|---|---|
| KR | 1020020034995 | 5/2002 |
| KR | 1020120031674 | 4/2012 |

*Primary Examiner* — Laura Martin
*Assistant Examiner* — Rose M Miller
(74) *Attorney, Agent, or Firm* — Cantor Colburn LLP

(57) ABSTRACT

Provided are an apparatus and a method for measuring a nonlinearity parameter using laser, and more particularly, an apparatus and a method for measuring a nonlinearity parameter using laser for computing the nonlinearity parameter by irradiating laser of a toneburst signal on a surface of a sample by non-contact type laser so as to excite the sample, irradiating measurement laser beam on the surface of the sample so as to receive displacement information occurring on the surface of the sample over time, measuring the displacement in an interferometer principle, and performing a bandpass filtering for the measured signal so as to measure amplitude $A_1$ of a component of a fundamental frequency and amplitude $A_2$ of a component of a secondary harmonic wave.

6 Claims, 7 Drawing Sheets

(51) Int. Cl.
*G01N 29/11* (2006.01)
*G01N 29/34* (2006.01)
*G01N 29/42* (2006.01)

(52) U.S. Cl.
CPC .......... *G01N 29/343* (2013.01); *G01N 29/42* (2013.01); *G01N 2291/02491* (2013.01)

(58) Field of Classification Search
CPC ................ G01N 29/343; G01N 29/42; G01N 2291/02491; G01N 2291/014; G01N 21/1704; G01N 21/1706; G01N 21/1708; G01N 21/1702; G01B 11/161; G01H 9/00; G01H 9/008; G01H 9/002
USPC .................................... 73/642, 643, 644, 579
See application file for complete search history.

(56) References Cited

U.S. PATENT DOCUMENTS

| | | | | |
|---|---|---|---|---|
| 2013/0314717 A1* | 11/2013 | Yi | .................... | G02B 21/0032 356/479 |
| 2014/0347462 A1* | 11/2014 | Schanne-Klein | .. | G02B 21/0032 348/79 |
| 2015/0160120 A1* | 6/2015 | Sun | .................... | G01N 21/1702 73/606 |

* cited by examiner

APPARATUS AND METHOD FOR MEASURING NONLINEARITY PARAMETER USING LASER

CROSS-REFERENCE TO RELATED APPLICATIONS

This application claims priority under 35 U.S.C. §119 to Korean Patent Application No. 10-2014-0022991, filed on Feb. 27, 2014, in the Korean Intellectual Property Office, the disclosure of which is incorporated herein by reference in its entirety.

TECHNICAL FIELD

The present invention relates to an apparatus and a method for measuring a nonlinearity parameter using laser, and more particularly, to an apparatus and method for measuring a nonlinearity parameter using laser for computing the nonlinearity parameter by irradiating laser of a toneburst signal on a surface of a sample using a non-contact type laser so as to excite the sample, irradiating a measurement laser beam on the surface of the sample so as to receive displacement information occurring on the surface of the sample over time, measuring the displacement in an interferometer principle, and performing a bandpass filtering for the measured signal so as to measure an amplitude $A_1$ of a component of a fundamental frequency and an amplitude $A_2$ of a component of a secondary harmonic wave.

BACKGROUND

A non-destructive inspection is performed to secure safety for quality of a product by checking whether or not the product has defect during the production, manufacturing or use of the product. For example, the non-destructive inspection is also performed to evaluate whether the product can be continuously used by checking a corrosion state, deterioration, whether or not a crack occurs, and the like.

A nonlinearity parameter is an ultrasonic technique capable of measuring material properties. Examples of a previously developed method for measuring the nonlinearity parameter include a capacitance measuring method and a piezoelectric receiving method. The above-mentioned methods may compute the nonlinearity parameter by measuring a displacement $A_1$ of a fundamental frequency and a displacement $A_2$ of a secondary harmonic wave.

Since the capacitance measuring method needs to prepare a test specimen having surface roughness of 1 to 2 μm and requires a complex calibration process for converting the measured signal into the components of a fundamental frequency and a secondary harmonic wave, it is very difficult to be used at the site.

The piezoelectric receiving method has a simpler calibration process than the capacitance measuring method, but has a problem in that a value of the computed nonlinearity parameter is varied depending on an attachment state of a probe and a kind and length of window at the time of a digital signal process.

Korean Patent Laid-Open Publication No. 10-2012-0031674 discloses a system and apparatus for measuring nonlinearity of an ultrasonic wave.

SUMMARY

An embodiment of the present invention is directed to an apparatus and a method for measuring a nonlinearity parameter using laser capable of each performing excitation and reception using non-contact laser by performing the excitation using a toneburst apparatus that generates a narrow band frequency by optically modulating continuous wave (CW) laser, and collecting a signal using a laser interferometer at the opposite side, in order to minimize error due to an attachment state of a probe or a signal processing.

In one general aspect of the present invention, an apparatus for measuring a nonlinearity parameter using laser includes: an exciting unit 100 irradiating laser of a toneburst signal on a surface of a sample 10 so as to excite the sample 10; a receiving unit 200 irradiating laser beam for measurement on the surface of the sample 10 on which the laser of the toneburst signal is irradiated from the exciting unit 100, using an interferometer and receiving displacement information occurring on the surface of the sample 10 over time; and a component measuring unit 300 performing a bandpass filtering for a signal received from the receiving unit 200 so as to measure an amplitude $A_1$ of a component of a fundamental frequency and an amplitude $A_2$ of a component of a secondary harmonic wave.

In another general aspect, a method for measuring a nonlinearity parameter using laser includes: an exciting operation S10 irradiating laser of a toneburst signal on a surface of a sample 10 so as to excite the sample 10; a receiving operation S20 irradiating laser beam for measurement on the surface of the sample 10 on which the laser of the toneburst signal is irradiated from the exciting operation S10, using an interferometer and receiving displacement information occurring on the surface of the sample 10 over time; and a component measuring operation S30 performing a bandpass filtering for a signal received from the receiving operation S20 so as to measure an amplitude $A_1$ of component of a fundamental frequency and an amplitude $A_2$ of component of a secondary harmonic wave.

Other features and aspects will be apparent from the following detailed description, the drawings, and the claims.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawings.

Figure 1:
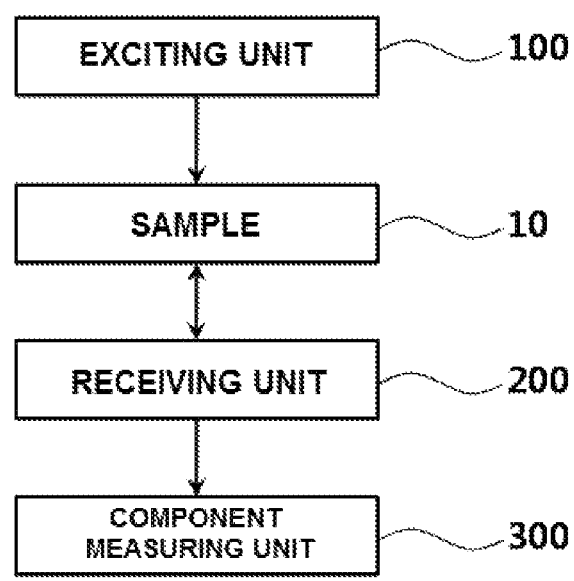
FIG. 1 is a block diagram of an apparatus for measuring a nonlinearity parameter using laser according to an exemplary embodiment of the present invention.
Figure 2:
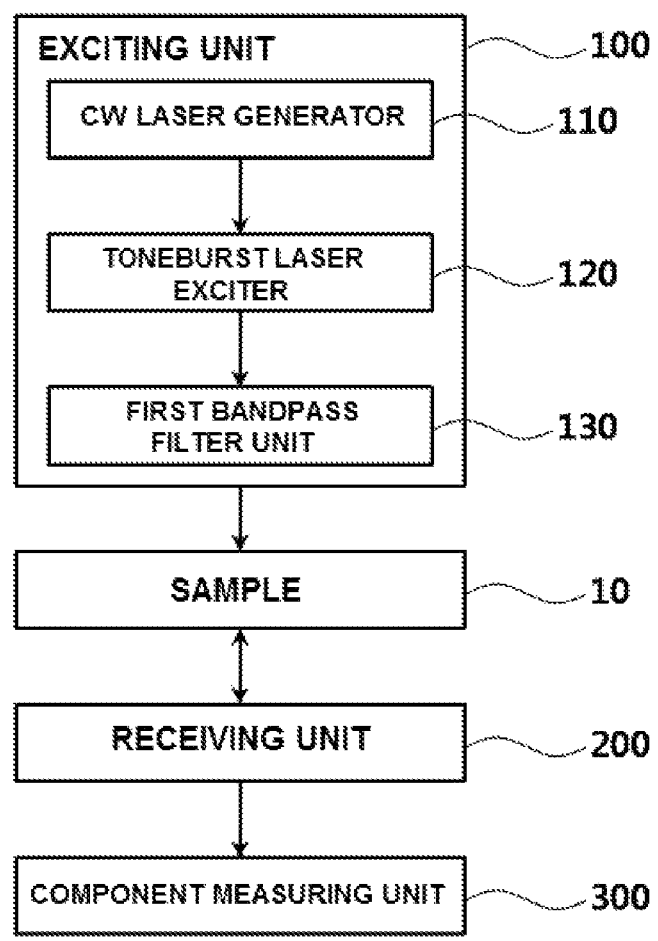
FIG. 2 is a block diagram specifically showing an exciting unit of FIG. 1.
Figure 3:
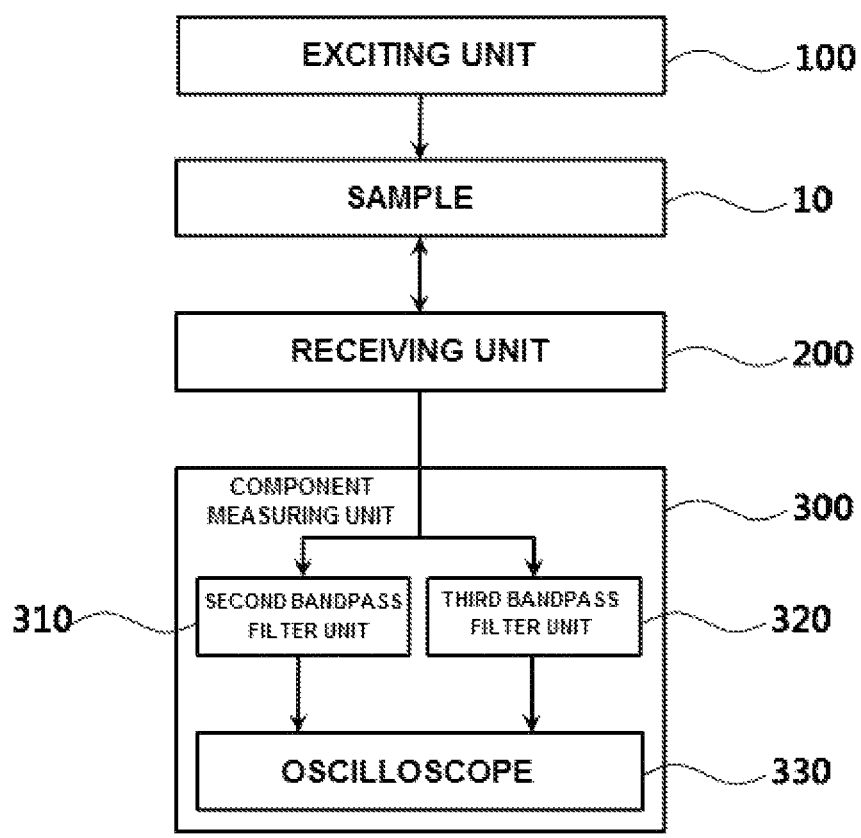
FIG. 3 is a block diagram specifically showing a component measuring unit of FIG. 1.
Figure 4:
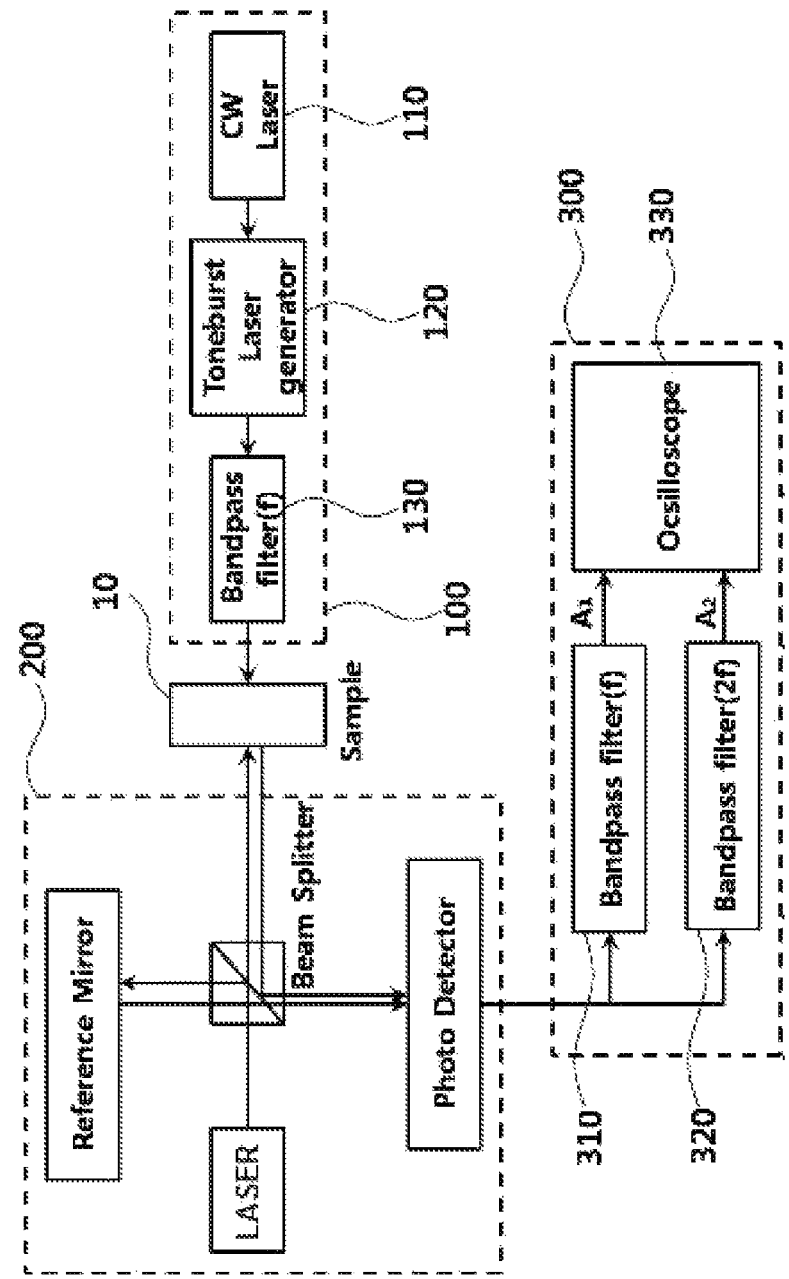
FIG. 4 is a concept diagram of the apparatus for measuring a nonlinearity parameter using laser according to an exemplary embodiment of the present invention.
Figure 5:
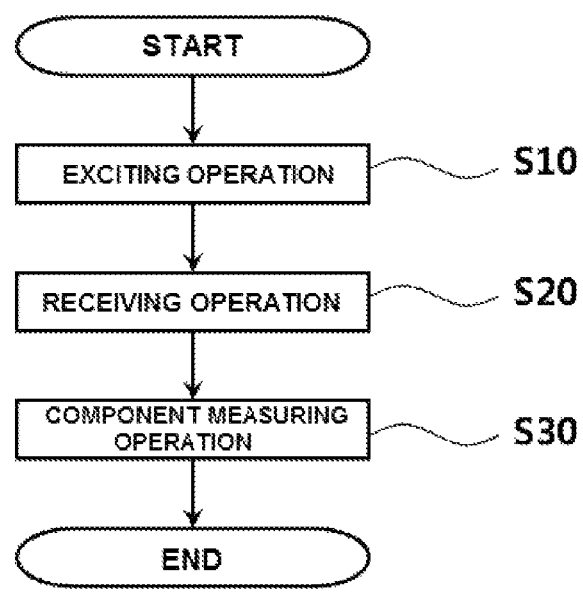
FIG. 5 is a flowchart of a method for measuring a nonlinearity parameter using laser according to an exemplary embodiment of the present invention.
Figure 6:
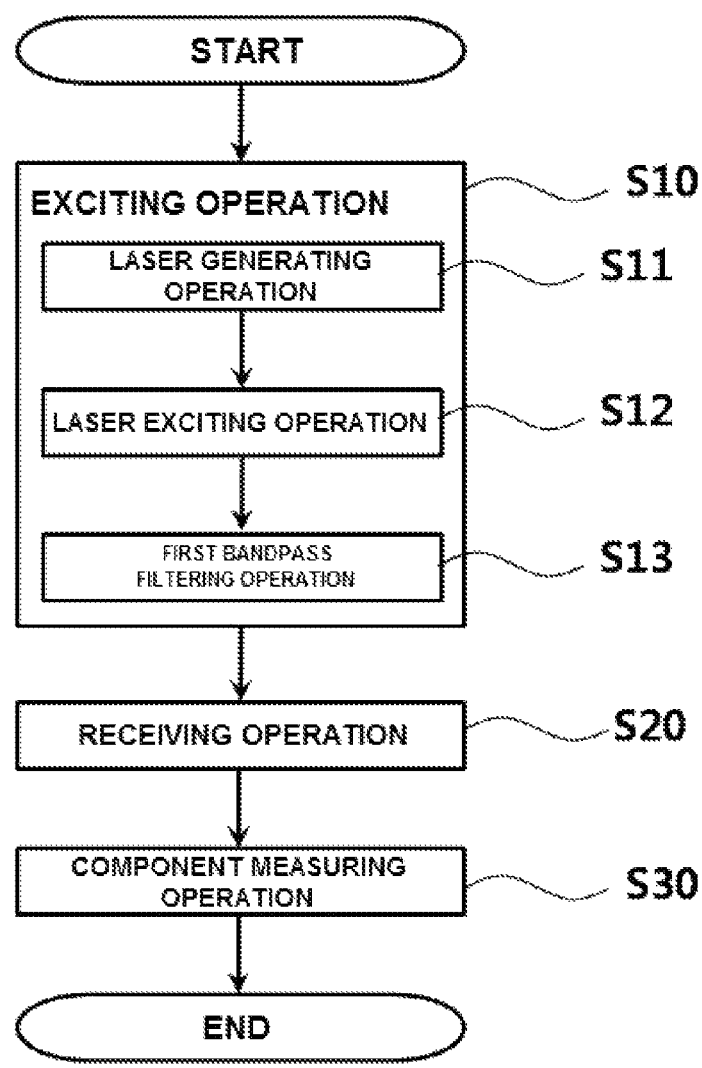
FIG. 6 is a flowchart specifically showing an excitation operation of FIG. 5.
Figure 7:
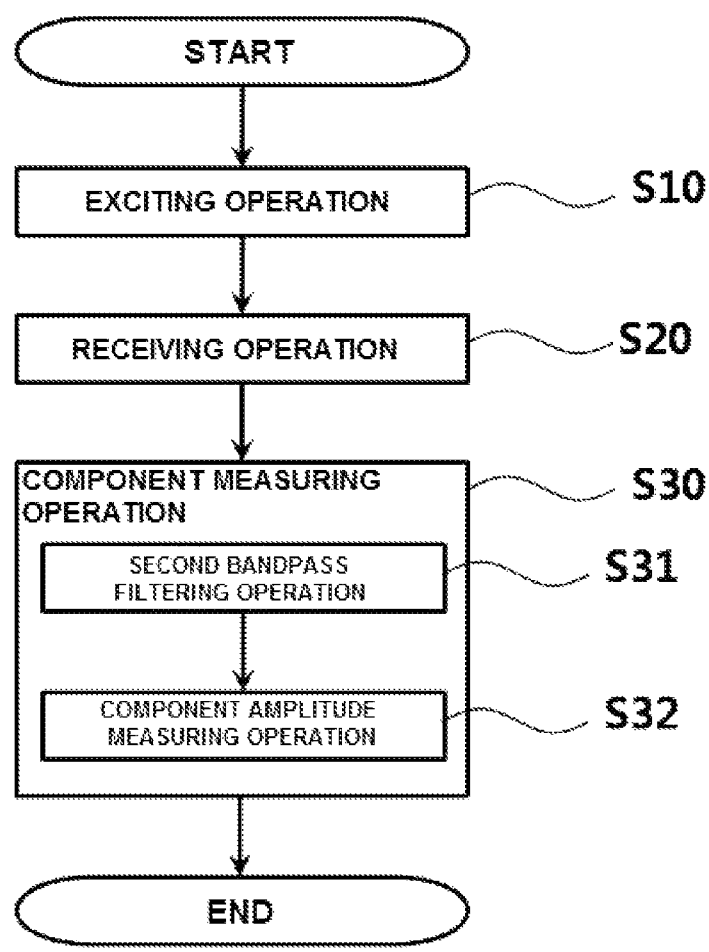
FIG. 7 is a flowchart specifically showing a component measuring operation of FIG. 5.

FIG. 1 is a block diagram of an apparatus for measuring a nonlinearity parameter using laser according to an exemplary embodiment of the present invention, FIG. 2 is a block diagram specifically showing an exciting unit of FIG. 1, FIG. 3 is a block diagram specifically showing a component measuring unit of FIG. 1, FIG. 4 is a concept diagram of the apparatus for measuring a nonlinearity parameter using laser according to an exemplary embodiment of the present invention, FIG. 5 is a flowchart of a method for measuring a nonlinearity parameter using laser according to an exemplary embodiment of the present invention, FIG. 6 is a flowchart specifically showing an excitation operation of FIG. 5, and FIG. 7 is a flowchart specifically showing a component measuring operation of FIG. 5.

As shown in FIG. 1, an apparatus for measuring a nonlinearity parameter using laser includes an exciting unit 100, a receiving unit 200, and a component measuring unit 300.

The exciting unit 100 irradiates laser of a toneburst signal on a surface of a sample 10 so as to excite the sample 10. Here, the terms "toneburst" means an adjustable sine wave burst for a test, and "tone" means a signal sound by a frequency of a range from 20 Hz to several MHz.

If laser of the toneburst signal is irradiated on the sample, the sample is excited and an ultrasound wave is propagated into the sample, and if the ultrasound wave arrives at the opposite side, a displacement occurs on a surface of the sample over time.

In other words, the exciting unit 100 excites the sample using a non-contact laser.

As shown in FIG. 2, the exciting unit 100 generating the laser of the toneburst signal will be described below in more detail.

The exciting unit 100 may include a continuous wave (CW) laser generator 110, a toneburst laser exciter 120, and a first bandpass filter unit 130.

The terms "CW laser" refers to laser that may be continuously oscillated at a constant output and may maintain a straight line output which is in parallel to a time axis on a graph of time and output.

The toneburst laser exciter 120 modulates the signal generated from the CW laser generator 110 into a toneburst signal.

In other words, the toneburst signal is generated by modulating the CW laser using the toneburst laser exciter 120. That is, a component of a fundamental frequency is excited.

The first bandpass filter unit 130 suppresses harmonic components of the signal output from the toneburst laser exciter 120.

In other words, the harmonic components of the laser of the toneburst signal may be suppressed by using the first bandpass filter unit 130.

As a result, since the signal having a desired frequency and wavelength may be generated by modulating the CW laser into the toneburst signal having a desired frequency using the toneburst laser exciter, and suppressing harmonic components using the first bandpass filter unit, it is possible to more accurately measure the nonlinearity parameter.

The receiving unit 200 irradiates laser beam for measurement on the surface of the sample 10 to which the laser of the toneburst signal is irradiated from the exciter 100, by using an interferometer, and receives displacement information occurring on the surface of the sample 10 over time.

As described above, if the laser of the toneburst signal is irradiated on the sample, the sample is excited and the ultrasound wave is propagated into the sample, and if the ultrasound wave arrives at the opposite side, the displacement occurs on the surface of the sample over time. The displacement is measured by using the interferometer.

The interferometer is used to measure a wavelength, precisely compare a length and a distance with each other, compare an optical distance, and so forth, and may be generally classified into two kinds, that is, an interference spectroscope and an interference refractometer. The interference spectroscope is an apparatus for observing a microstructure of a spectrum and generally uses multi-beam interference. The representative examples thereof include Fabry-Perot interferometer, Lummer-Gehrcke plate, Michelson's step-grating, and the like. The interference refractometer, which is an apparatus for precisely calculating a difference in the light path causing interference by measuring positions of interference fringes and measuring a refractive index of gas using the difference of the light path, uses interference between two rays. The representative examples thereof include Rayleigh's interferometer, Jamin interferometer, and the like, including Michelson interferometer.

In this case, the above-mentioned interferometers may use the Michelson interferometer or Laser Doppler vibrometer.

The Michelson interferometer, which is an interferometer (see FIG. 4) configured of a dielectric thin plate (beam splitter) having anti-reflectivity, a fixed reflective plate (reference mirror), and a movable reflective plate (sample), is an apparatus for accurately measuring a millimeter-wave frequency. A phase difference of the wave, which is reflected by the two reflective plates and is input to a receiver, is changed between 0° and 180° by moving the movable reflective plate to change a position thereof, and consequently, the input of the receiver may also be changed between the maximum and the minimum. Thereby, a wavelength and a frequency of the wave are obtained.

In other words, the nonlinearity parameter may be more accurately measured by using the Michelson interferometer.

However, in the case where it is difficult to install the Michelson interferometer, the Laser Doppler vibrometer may be used. Since the Laser Doppler vibrometer is available from a regular corporation (e.g., Polytec, and the like), it may be easily installed in the apparatus, and may be a practical method when the measurement is performed at the real site.

The component measuring unit 300 measures an amplitude $A_1$ of a component of the fundamental frequency and an amplitude $A_2$ of a component of the secondary harmonic wave by performing a bandpass filtering for the signal received from the receiving unit 200.

As shown in FIG. 3, the component measuring unit 300 that measures the amplitude $A_1$ of the component of the fundamental frequency and the amplitude $A_2$ of the component of the secondary harmonic wave will be described below in more detail.

The component measuring unit 300 may include a second bandpass filter unit 310, a third bandpass filter unit 320, and an oscilloscope 330.

The second bandpass filter unit 310 extracts the component of the fundamental frequency of the signal measured from the receiving unit 200.

The third bandpass filter unit 320 extracts the component of the secondary harmonic wave of the signal measured from the receiving unit 200.

The oscilloscope 330 measures amplitudes of the respective components that pass through the second bandpass filter unit 310 and the third bandpass filter unit 320.

That is, the amplitude $A_1$ of the component of the fundamental frequency and the amplitude $A_2$ of the component of the secondary harmonic wave may be measured by performing the bandpass filtering for the measured signal.

In other words, since the amplitude of the component of the fundamental frequency and the amplitude of the component of the secondary harmonic wave may be simultaneously measured by using the respective bandpass filter units, it is possible to more accurately measure the nonlinearity parameter in real time.

The apparatus for measuring a nonlinearity parameter using laser according to an exemplary embodiment of the present invention may further include a nonlinearity parameter measuring unit for measuring the nonlinearity parameter using the measured values from the component measuring unit 300.

The nonlinearity parameter, which is an ultrasonic wave technique capable of measuring material properties, may be measured as expressed in the following Equation.

$$\beta = \frac{8}{k^2 x} \frac{A_2}{A_1^2}$$

(where $A_1$ denotes an amplitude of a component of a fundamental frequency, $A_2$ denotes an amplitude of a component of a secondary harmonic wave, k denotes a wave number, and x denotes a length of a sample)

According to the piezoelectric receiving method, the measurements of the nonlinearity parameter may be varied depending on the attachment state of the probe. However, in the case where the apparatus for measuring a nonlinearity parameter using laser according to an exemplary embodiment of the present invention is used, since there is no need to directly contact the probe with the specimen, measurement repeatability may be maintained and measurement reliability may be improved.

In addition, since pipes in nuclear plants and power plants are operated in a high temperature environment of 200 to 300° C., the probe that may be operated at the above-mentioned temperature is required and an ambient temperature probe may not be applied thereto. However, in the case where the apparatus for measuring a nonlinearity parameter using a laser according to an exemplary embodiment of the present invention is used, since the excitation and reception are performed in the non-contact method, the present invention may be utilized in a high temperature facility.

In addition, in the case where some of the pipes and structures of a power generating unit are in a remote area where it is difficult for people to access, there are cases in which it is impossible to install an experiment apparatus. Therefore, in the case in which the apparatus for measuring a nonlinearity parameter using a laser according to an exemplary embodiment of the present invention is used, the nonlinearity parameter of the structures installed even in the above-mentioned area may be measured.

As shown in FIG. 5, a method for measuring a nonlinearity parameter using a laser according to an exemplary embodiment of the present invention includes an exciting operation S10, a receiving operation S20, and a component measuring operation S30.

In the exciting operation S10, laser of a toneburst signal is irradiated on a surface of a sample 10 so as to excite the sample 10.

If the laser of the toneburst signal is irradiated on the sample, the sample is excited and an ultrasound wave is propagated into the sample, and if the ultrasound wave arrives at the opposite side, a displacement occurs on a surface of the sample over time.

As shown in FIG. 6, the exciting operation S10 generating the laser of the toneburst signal will be described below in more detail.

The exciting operation S10 may include a laser generating operation S11, a toneburst laser exciting operation S12, and a first bandpass filtering operation S13.

In the laser generating operation S11, continuous wave (CW) laser is generated.

The CW laser may maintain a straight line output which is in parallel to a time axis, that is, a constant output, on a graph of time and output.

In the toneburst laser exciting operation S12, the signal generated from the laser generating operation S11 is modulated into a toneburst signal.

In first bandpass filtering operation S13, a harmonic component of the signal output from the laser exciting operation S12 is suppressed.

That is, since the signal having a desired frequency and wavelength may be generated by modulating the CW laser having a constant output into the toneburst signal having a desired frequency by the toneburst laser exciting operation S12 and suppressing harmonic components by the first bandpass filtering operation S13, it is possible to more accurately measure the nonlinearity parameter.

In the receiving operation S20, laser beam for measurement is irradiated on the surface of the sample 100 to which the laser of the toneburst signal is irradiated from the exciting operation S10, by using an interferometer, and displacement information occurring on the surface of the sample 10 over time is received.

As described above, if the laser of the toneburst signal is irradiated on the sample, the sample is excited and the ultrasound wave is propagated into the sample, and if the ultrasound wave arrives at the opposite side, the displacement occurs on the surface of the sample over time. The displacement is measured by using the interferometer.

In this case, the above-mentioned interferometers may use the Michelson interferometer or the Laser Doppler vibrometer.

In the component measuring operation S30, an amplitude $A_1$ of the component of the fundamental frequency and an amplitude $A_2$ of the component of the secondary harmonic wave are measured by performing a bandpass filtering for the signal received from the receiving operation S20.

As shown in FIG. 7, the component measuring operation S30 that measures the amplitude $A_1$ of the component of the fundamental frequency and the amplitude $A_2$ of the component of the secondary harmonic wave will be described below in more detail.

The component measuring operation S30 may include a second bandpass filtering operation S31 and a component amplitude measuring operation S32.

In the second bandpass filtering operation S31, the component of the fundamental frequency and the component of the secondary harmonic wave of the signal measured from the receiving operation S20 are extracted.

In the component amplitude measuring operation S32, the amplitudes of the components of the fundamental frequency and the secondary harmonic wave extracted by the second bandpass filtering operation S31 are measured.

That is, since the amplitude of the component of the fundamental frequency and the amplitude of the component of the secondary harmonic wave may be simultaneously measured by the second bandpass filtering operation S31, it is possible to more accurately measure the nonlinearity parameter in real time.

The method for measuring a nonlinearity parameter using laser according to an exemplary embodiment of the present invention may further include a nonlinearity parameter measuring operation for measuring the nonlinearity parameter using the measured values from the component measuring operation S30.

The nonlinearity parameter, which is an ultrasonic technique capable of measuring material properties, may be measured as expressed in the following Equation.

$$\beta = \frac{8}{k^2 x} \frac{A_2}{A_1^2}$$

(where $A_1$ denotes an amplitude of a component of a fundamental frequency, $A_2$ denotes an amplitude of a component of a secondary harmonic wave, k denotes a wave number, and x denotes a length of a sample)

Hereinabove, although the method for measuring a nonlinearity parameter using a laser according to an exemplary embodiment of the present invention has been described, it will be easily understood by those of ordinary skill in the art that the method for measuring a nonlinearity parameter using laser described above may also be provided so as to be included in a computer-readable recording medium by tangibly implementing a program of instructions for implementing the method. In other words, the method for measuring a nonlinearity parameter using laser according to an exemplary embodiment of the present invention is implemented in a form of program instructions capable of being performed through various computer components so as to be recordable in the computer-readable recording medium. The computer readable recording medium may include program instructions, data files, data structure, or the like, alone or in a combination thereof. The program instructions recorded in the computer-readable recording medium may be designed and configured especially for the present invention, or may be known to those skilled in a field of computer software. Examples of the computer-readable recording medium may include a magnetic medium such as a hard disk, a floppy disk, and a magnetic tape; an optical media such as a CD-ROM and a DVD; a magneto-optical media such as a floptical disk; and a hardware device specially constituted to store and perform program instructions such as a ROM, a RAM, a flash memory, a USB memory, or the like. The computer-readable recording medium may also be a transmission medium such as a light or metal line, a waveguide, or the like including a carrier transmitting a signal specifying program instructions, data structures, and the like. Examples of program instructions include machine language codes such as being made by compilers as well as high-level language codes capable of being executed by computers using interpreters, or the like. The hardware device may be constituted to be operated as one or more software modules in order to perform the operation according to the present invention, and vice versa.

As set forth above, according to the exemplary embodiment of the present invention, since the apparatus and method for measuring a nonlinearity parameter using laser do not use the probe which is separately attached, by each performing the excitation and the reception using the non-contact laser, the apparatus and method for measuring a nonlinearity parameter using laser may be used at the site without being significantly affected by the surface state of specimen, the attachment state of the probe, and the kind and length of window at the time of the digital signal processing that are problems of an existing method occurring due to the attachment state of the probe or at the time of a signal processing, whereby measurement repeatability may be maintained and measurement reliability may be improved, thereby making it possible to accurately measure the nonlinearity parameter.

In addition, since the excitation and the reception are performed in the non-contact method, the present invention may be utilized in the high temperature facility.

In addition, even in the case in which the high temperature facility is in a remote area where it is difficult for people to access and consequently, it is impossible to install an experimental apparatus therein, the nonlinearity parameter may be measured.

In addition, since the signal having a desired frequency and length may be generated by modulating the CW laser into the toneburst signal having the desired frequency using the toneburst laser exciter and suppressing the harmonic components using the first bandpass filter unit, it is possible to more accurately measure the nonlinearity parameter.

In addition, it is possible to more accurately measure the nonlinearity parameter using Michelson interferometer, and in the case in which it is difficult to install the Michelson interferometer, the apparatus may be easily built using a laser Doppler interferometer.

Further, since the amplitude of the component of the fundamental frequency and the amplitude of the component of the secondary harmonic wave may be simultaneously measured by using the respective bandpass filter units, it is possible to more accurately measure the nonlinearity parameter in real time.

The present invention is not limited to the above-mentioned exemplary embodiments, and may be variously applied, and may be variously modified without departing from the gist of the present invention claimed in the claims.

What is claimed is:

1. An apparatus for measuring a nonlinearity parameter using laser, the apparatus comprising:
    an exciting unit irradiating laser of a toneburst signal on a surface of a sample so as to excite the sample;
    a receiving unit irradiating laser beam for measurement on the surface of the sample on which the laser of the toneburst signal is irradiated from the exciting unit, using an interferometer, and receiving displacement information occurring on the surface of the sample over time;

a component measuring unit performing a bandpass filtering for a signal received from the receiving unit so as to measure a first amplitude of a component of a fundamental frequency and a second amplitude of a component of a secondary harmonic wave, wherein the component measuring unit includes:

a first bandpass filter unit extracting the component of the fundamental frequency of the signal measured from the receiving unit;

a second bandpass filter unit extracting the component of the secondary harmonic wave of the signal measured from the receiving unit; and an oscilloscope measuring the first amplitude of the component of the fundamental frequency and the second amplitude of the component of the secondary harmonic wave that pass through the first bandpass filter unit and the second bandpass filter unit; and a nonlinearity parameter measuring unit for measuring the nonlinearity parameter using the measured first amplitude and the measured second amplitude from the component measuring unit.

2. The apparatus of claim 1, wherein the exciting unit includes:

a continuous wave (CW) laser generator;

a toneburst laser exciter modulating a signal generated from the CW laser generator into the toneburst signal; and a third bandpass filter unit suppressing harmonic components of a signal output from the toneburst laser exciter.

3. The apparatus of claim 1, wherein the interferometer uses a Michelson interferometer or a laser Doppler vibrometer.

4. A method for measuring a nonlinearity parameter using laser, the method comprising:

an exciting operation irradiating laser of a toneburst signal on a surface of a sample so as to excite the sample;

a receiving operation irradiating laser beam for measurement on the surface of the sample on which the laser of the toneburst signal is irradiated from the exciting operation, using an interferometer, and receiving displacement information occurring on the surface of the sample over time;

a component measuring operation performing a bandpass filtering operation for a signal received from the receiving operation so as to measure a first amplitude of a component of a fundamental frequency and a second amplitude of a component of a secondary harmonic wave, wherein the bandpass filtering operation includes:

a first bandpass filtering operation extracting the component of the fundamental frequency of the signal measured from the receiving operation;

a second bandpass filtering operation extracting the component of the secondary harmonic wave of the signal measured from the receiving operation; and a component amplitude measuring operation measuring the first amplitudes of the component of the fundamental frequency and the second amplitude of the component of the secondary harmonic wave; and a nonlinearity parameter measuring operation for measuring the nonlinearity parameter using the measured first amplitude and the measured second amplitude from the component measuring operation.

5. The method of claim 4, wherein the exciting operation includes:

a laser generating operation generating continuous wave (CW) laser;

a toneburst laser exciting operation modulating a signal generated from the laser generating operation into the toneburst signal; and a third bandpass filtering operation suppressing harmonic components of a signal output from the toneburst laser exciting operation.

6. The method of claim 4, wherein the interferometer uses a Michelson interferometer or a laser Doppler vibrometer.

* * * * *